United States Patent [19]
Meltzer

[11] Patent Number: 5,582,798
[45] Date of Patent: Dec. 10, 1996

[54] VOLUME SENSING DEVICE

[75] Inventor: Walter Meltzer, New Milford, Conn.

[73] Assignee: Cyberlab Inc., Brookfield, Conn.

[21] Appl. No.: 394,256

[22] Filed: Feb. 23, 1995

[51] Int. Cl.$^6$ .................................................. G05D 9/12
[52] U.S. Cl. ...................... 422/100; 422/106; 73/304 C; 73/864.24; 73/864.25; 340/620; 324/664; 324/671; 324/689
[58] Field of Search ............................ 422/100, 99, 106; 73/864.24, 864.25, 304 C; 340/620; 324/664, 671, 689

[56] References Cited

U.S. PATENT DOCUMENTS

| | | | |
|---|---|---|---|
| 3,253,458 | 5/1966 | Katz et al. | 324/664 |
| 4,677,522 | 6/1987 | Persson | 73/304 C |
| 4,749,988 | 6/1988 | Berman et al. | 73/304 C |
| 5,012,683 | 5/1991 | Davis | 73/304 C |
| 5,270,210 | 12/1993 | Weyrauch | 422/100 |
| 5,423,206 | 6/1995 | Hetzel | 73/304 C |
| 5,465,619 | 11/1995 | Sotack et al. | 324/664 |

*Primary Examiner*—Jill Warden
*Assistant Examiner*—Alexander Markoff
*Attorney, Agent, or Firm*—Klein & Vibber P.C.

[57] ABSTRACT

A volume sensing device for determining the volume of liquid present in a standard plastic disposable pipette during a pipetting operation, which operation can be an aspiration or dispensing of liquid. The device comprises a cylinder made of hard synthetic material into which a disposable pipette is lowered at a predetermined velocity. The pipette which is being lowered into the cylinder holds an amount of liquid the volume of which the volume sensing device approximately determines. A pair of metal rings are coaxially mounted near the top end of the plastic cylinder. The pair of metal rings are preferably mounted in mating machined recesses of the plastic cylinder. This pair of metal rings is separated from each other by a small gap which forms the dielectric material of a capacitative circuit when the upper ring is connected to one portion of this circuit and the lower ring is connected to an other portion of the capacitative circuit. Below the pair of rings the plastic cylinder forms a blind bore of substantially larger axial length than the axial length of the pair of rings. The pair of rings and the blind bore of the cylinder have equal internal diameters. The upper ring of the pair of rings is connected to a pulse generator and the lower ring is connected to a circuit including an amplifier and a comparator, which circuit is connected to a computer data storage device.

8 Claims, 5 Drawing Sheets

VOLUME SENSING DEVICE

BACKGROUND OF THE INVENTION

The invention relates to a volume sensing device for approximately determining the volume of liquid present in, for example, a plastic disposable pipette. A large variety of pipetting operations find many applications in medicine and industry. For example, pipetting operations are used in various medical and chemical testing and analyzing procedures during which the volume of liquid present in a pipette or probe tip used in the pipetting operation needs to be closely monitored. Such a multiple pipetting operation can, for example, be carried out by a device such as described in the co-assigned U.S. Pat. Nos. 5,055,263 and 5,036,510 entitled AUTOMATED PIPETTING SYSTEM (hereinafter the "Meltzer Robot") and a device of the type disclosed in U.S. Pat. No. 4,979,093.

The volume sensing device of this invention has as one of its objects to verify the approximate volume present in the pipette tip during the pipetting operation and, if such volume deviates from a preset value, the volume sensing device emits a signal which can be detected by the data storage device of a computer connected to the volume sensing device. The signal emitted by the volume sensing device may also trigger the energizing of an alarm, such as an alarm light, for example an LED mounted in the volume sensing device.

Pipetting devices of the state of the art frequently malfunction. For example, worn syringes, leaky connections and defective disposable pipette tips or probe tips may cause malfunctioning. Also, in case blood is the liquid which is being aspirated or dispensed, clotting or coagulation of the blood may occur in the pipette tip which causes a malfunctioning of the Automated Pipetting System

SUMMARY OF THE INVENTION

The principal object of the invention is to provide a device which is particularly designed for detecting a deviation from a preset volume value of liquid in a pipette or probe tip. In the state of the art volume sensing devices the sensing by means of a capacitative circuit was carried out by sensing the level of the liquid surface in a stationary vial, glass tube or other type of container. Such a known technique has the drawback that, with a small volume in a relatively large diameter vial, glass tube or vessel, the decrease of the liquid level to be detected is too small to be even coarsely measured in view of the coarse sensitivity of the state of the art level detection circuit. Even with larger volumes and smaller vials, glass tubes or vessels this prior art technique is not dependable due to errors that can be introduced by foam or babbles present in the liquid retained in the pipette or probe tip.

The volume sensing device of this invention provides a simple method for checking the actual volume present in a probe or disposable pipette tip. The accuracy of the device is about±20% without temperature drift compensation or computer enhancement. If the computer to which the device is the accuracy of data emitted by the Capacitative circuit of the device, the accuracy will improve to about 5% of the volume of a full pipette tip. On smaller configuration volumes as low as 5 µl can be reliably read without computer enhancement and a volume as low as 1 µl can be reliably read with computer enhancement. The volume sensing device of the invention operates satisfactorily with aqueous solutions, as well as organic solvents including non conductive solutions such as trichloroethane and hexane. While the sensitivity of the device is slightly less with non conductive solutions, the device can be adjusted to compensate for the type of liquid which is being used in the pipetting operation.

The volume sensing device of the invention uses a capacitative circuit for automatically detecting a substantial volume deviation from a predetermined volume of liquid present in a pipette or probe tip. A substantial change of volume causes a detectable change in the dielectric constant of a capacitative circuit as the pipette or probe tip holding a predetermined amount of liquid is axially inserted in a cylinder forming part of the volume sensing device. The underlying physical principle on which the invention is based is that a liquid suspension is a better conductor of electromagnetic waves than air. This is opposed to the conduction of direct current through a liquid varies with the type of liquid. For example, Hexane or Tri-Chloroethane are considered "poor" conductors compared to an aqueous solution. The use of a capacitative circuit has the additional advantage of being non-invasive. The capacitative circuit of the invention my essentially operate in three different modes of which only one is described in detail herein below.

Method 1

This method uses an automated pipetting system of the type disclosed in the Meltzer Robot wherein a pipette or probe is movable along a z-axis. The computer drive Meltzer Robot has means for indicating the Z-axis position in response to a signal generated by the Level Sensing Device of the Meltzer Robot. This method can be carried out in two ways. Both of the described methods require, however, a calibration prior to operation of the method in order to establish a relationship of the axial position of the movable probe in the plastic cylinder of the Volume Sensing Device.

A Calibration

A volume of liquid is first drawn into the probe or pipette tip by known aspiration means such as a syringe. The probe or pipette tip is then lowered a predetermined axial distance into the plastic cylinder forming part of the volume sensing device by means of a first command signal fed into the Meltzer Robot. The probe is then relatively slowly moved axially upward in the plastic cylinder according to a second input signal fed into the Meltzer Robot by means of a keyboard stroke or operation of the mouse of the computer. When the probe reaches an axial position, which changes the dielectric constant of the capacitative circuit a predetermined amount, the computer generates a trigger signal (which may include the triggering of an LED circuit) indicating that the top level of the liquid was at the trigger point of the volume sensing device. In this manner the axial position along the Z-axis of the trigger point is established. The probe is then withdrawn by the Meltzer Robot moving it axial upwardly along the Z-axis out of the plastic cylinder and expelling a predetermined amount of liquid from the probe. The computer of the Meltzer Robot then emits a signal which causes the probe to again be axially lowered into the plastic cylinder to the prior axial position and the capacitative circuit then checks for the absence of the liquid which has been removed from the probe, i.e. that no more liquid is present in the probe by measuring the change in dielectric constant. This calibration and/or test is performed automatically excepts for the step of adjusting for the axial distance of travel of the probe. to set the calibration point.

B. Operation

After the trigger depth for a predetermined probe volume has been established the volumes sensing device is ready to be used to detect whether the predetermined probe volume is present in the pipettes used, for example, in an automated pipetting operation. In such a pipetting operation a liquid sample is aspirated into the pipette tip and the pipette is then lowered into the plastic cylinder by means of the Meltzer Robot along the Z-axis to the predetermined trigger depth. If the capacitative circuit of the volume sensing device indicates the presence of liquid in the probe by the emission of the trigger signal, this indicates that the level of the liquid in the probe is at the trigger point of the volume sensing device previously established in step A thereby determining that the correct amount of liquid is present in the probe or pipette tip.

In order to check for a different volume level in the probe the computer is adjusted accordingly to establish a different trigger depth based on the diameter and taper of the pipette tip.

Method 2

A Calibration

A volume of liquid is aspirated into the pipette tip and then the probe is axially lowered into the maximum depth of the plastic cylinder of the volume sensing device. Thereafter the probe is slowly moved axially upwardly out of the plastic cylinder by same computer controlled mechanical device which is controlled by, for example, a mouse or computer keyboard of, for example, the Meltzer Robot, until the energizing circuit of an LED of the volume sensing device is triggered to indicate that the top level of the liquid in the pipette or probe tip has reached the trigger point of the capacitative circuit in the plastic cylinder of the volume sensing device.

B. Operation

The trigger depth for a predetermined volume is now known. After an undetermined quantity of liquid is aspirated into the pipette tip a command signal from the computer causes the probe to axially move to a maximum depth in the plastic cylinder of the volume sensing device and then again move axially upwardly out of the plastic cylinder until the capacitative circuit is triggered, which trigger signal is amplified by the capacitative circuit and is then received by the computer which then converts the received signal into a digital readout which indicates the volume of the liquid present in the pipette tip based on the trigger depth and the diameter and taper of the pipette tip.

BRIEF DESCRIPTION OF THE DRAWINGS

With these and other objects in view, which will become apparent in the following detailed description the present invention, which is shown by example only, will be clearly understood in connection with the accompanying drawing, in FIG. 1 is a plan view of the volume sensing device as seen from above the device.

DESCRIPTION OF THE PREFERRED EMBODIMENTS

Figure 1:
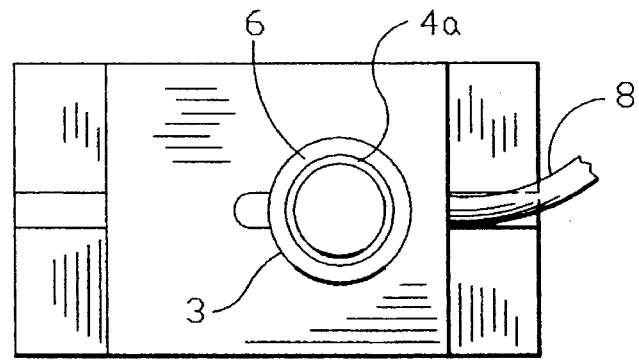
Figure 2:
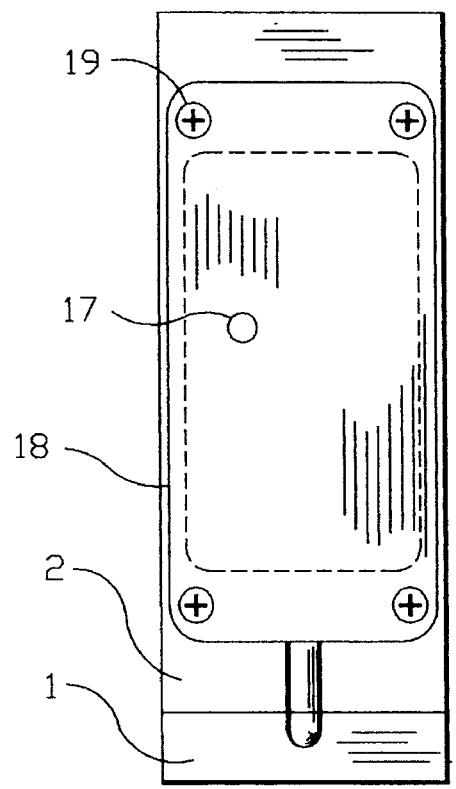
FIG. 2 is a rear elevational view as seen from the rear of the volume sensing device with a cover plate in place.
Figure 3:
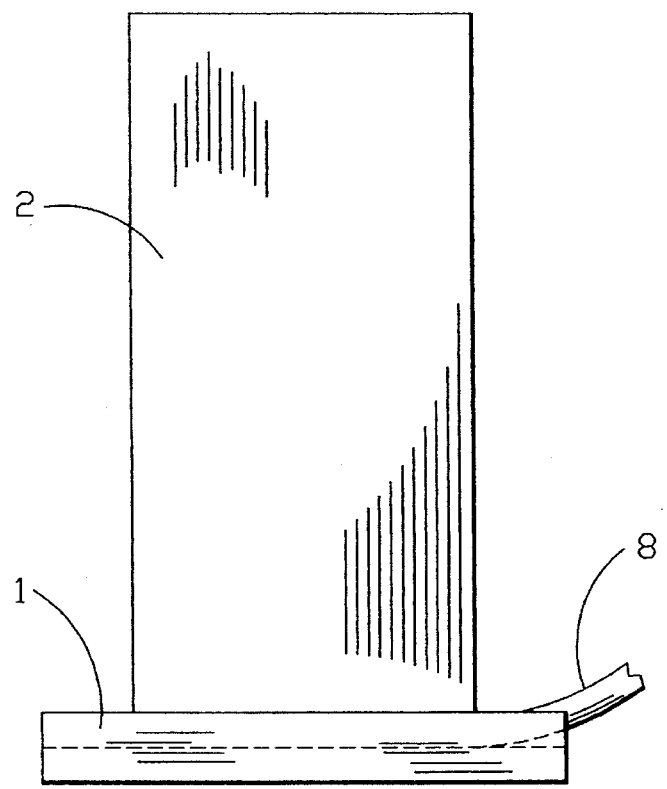
FIG. 3 is a side elevational view at a right angle from the rear elevational view of FIG. 2.
Figure 4:
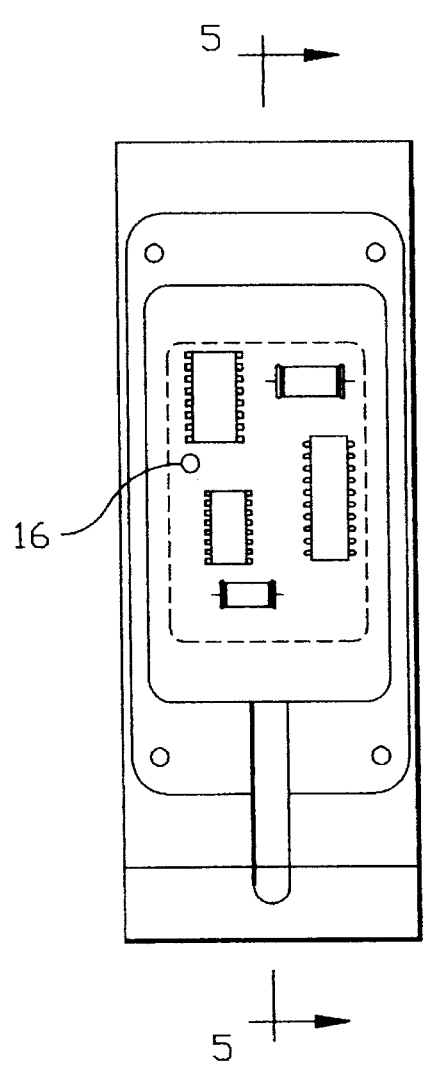
FIG. 4 is a rear elevational view similar to the view of FIG. 2 but with the cover plate removed so that the circuitry of the capacitative circuit of the volume sensing device can be seen.

Referring new to the drawing there is illustrated in FIGS. 1–5 the volume sensing device of the invention. The device includes a base plate 1 on Which there is mounted a housing 2. The base plate 1 and housing 2 are preferably made of aluminium. The housing 2 has a vertically extending blind bore 3. A cylinder 6 made of hard plastic material is tightly mounted in the blind bore 3. A pair of metal rings 4a and 4b are machined into the plastic cylinder 6, but can also be loosely mounted or even glued into the plastic cylinder 6, as long a they are maintained in a fixed predetermined position in the plastic cylinder 6. The pair of metal rings 4a and 4b have preferably internal diameters which are equal to the internal diameter of the plastic cylinder 6 so that the entire assembly of the pair of rings 4a and 4b and the plastic cylinder 6 present a continuous blind bore with a uniform internal diameter. This cylinder 6 is adapted to receive a standard plastic disposable pipette tip 8 which is axially automatically inserted in the plastic cylinder 6 manually or by mechanical means such as, for example, the Meltzer Robot.

A standard glass vial or tube 10 may optionally be mounted in the cylinder 6 on an axially upwardly extending plastic post 11 prior to initiation of an automated pipetting operation to ensure that no contaminating liquid, which may accidentally spill from the pipette tips during an automated pipetting operation, soils the internal walls of the blind bore.

Figure 5:
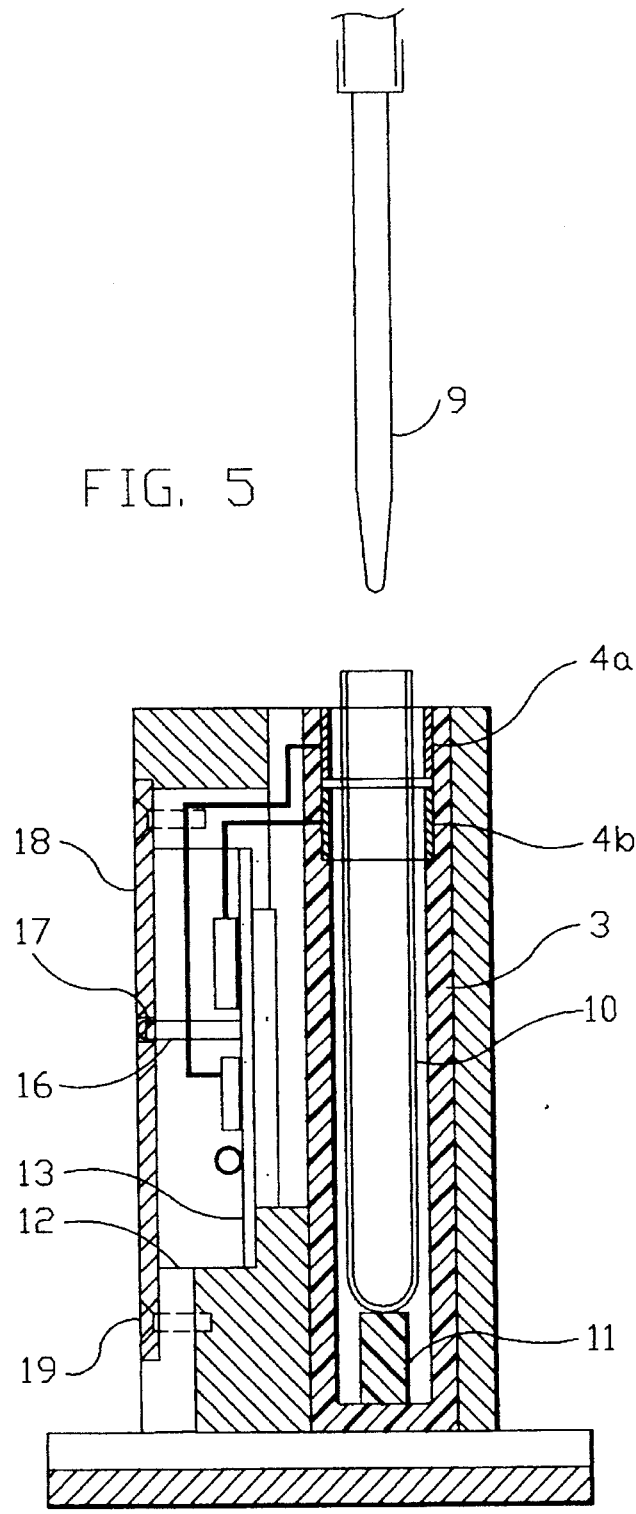
FIG. 5 is a cross sectional view along line 5—5 of FIG. 4.
Figure 6:
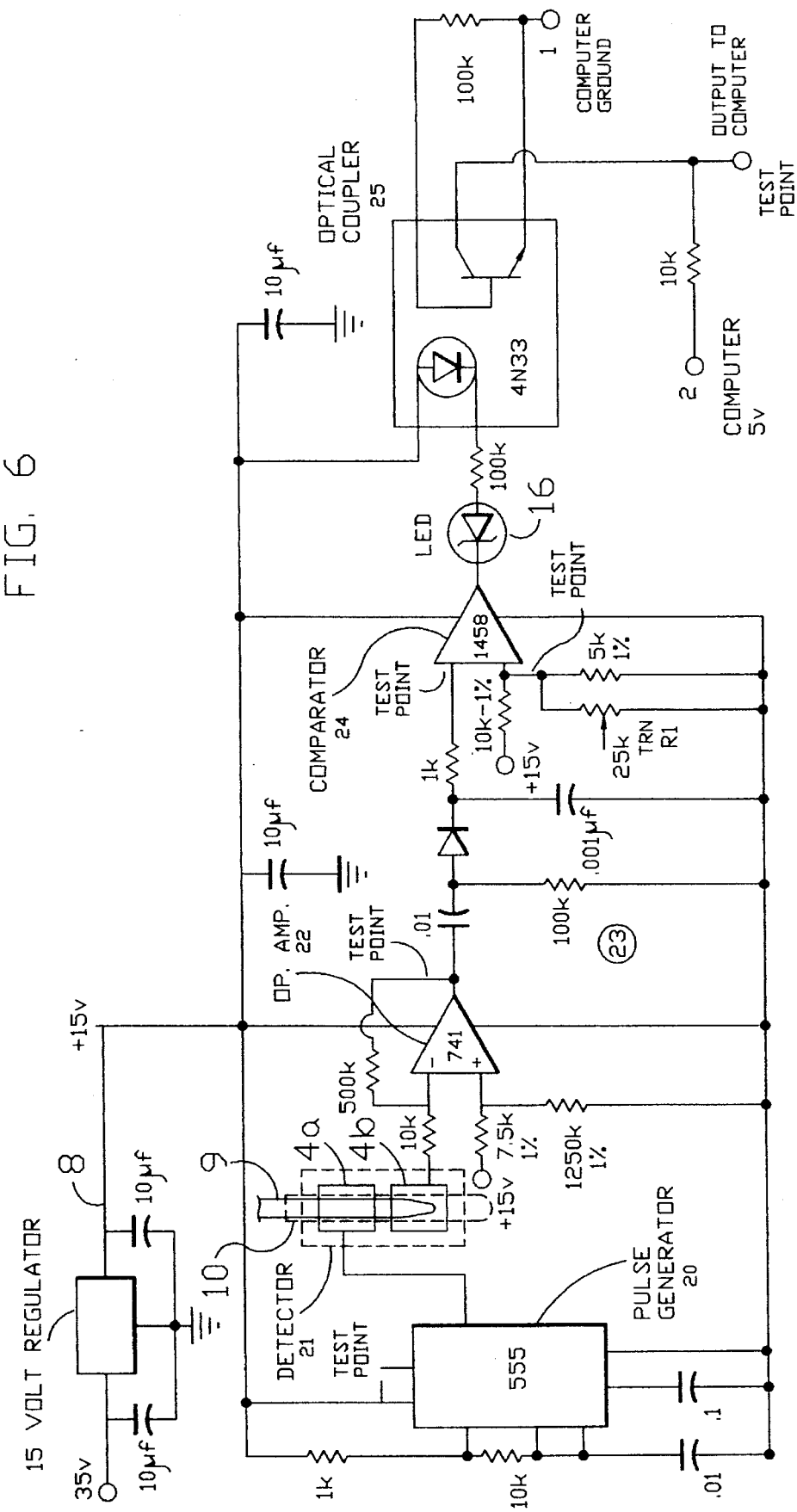
FIG. 6 is a circuit diagram of the capacitative circuit of the volume sensing device of the invention.

The circuitry of the volume sensing device is mounted on a board 13 which is mounted in a recess 12 disposed in the rear of the housing 2. The board 13 is mounted by four screws 14 against the vertical wall 15 of the recess 12. The pulse generator of the capacitative circuit is connected to the upper ring 4a and the operational amplifier is connected to the lower ring 4b, as is illustrated in FIGS. 5 and 6. The board 13 also supports an LED 16. The recess 12 is covered by a rear plate 18 which is mounted on the housing 2 by means of four screws 19 so that the housing, when fully assembled, presents a smooth parallelepiped. A hole 17 is provided in the rear plate 18, which hole is in alignment with the LED 16 so that when the LED 16 is lit the light from the LED 16 can be observed through the hole 17 by the operator of the device. The capacitative circuit is energized by means of an electrical energy source (not illustrated) which is connected to the capacitative circuit by means of a standard electrical cable 8 which is disposed in a recess of the base plate 1.

Manner of Operation

The manner of operation of the device is illustrated in FIGS. 5 and 7a to 7d. In FIG. 5 the pipette or probe tip 9 is in the position to calibrate the device for the Zero position (in this position the device can also be calibrated to compensate for the conductivity of the glass tube 10 in the event a glass tune is to be used in the automated pipetting operation). In this position the capacitative circuit is in condition to be calibrated. The pipette or probe tip 9 is empty and is positioned above the glass vial or tube 10. While the assembly is in the position illustrated in FIG. 5 the Zero point of the circuit can he calibrated and stored in the computer (not illustrated).

Figure 7A:
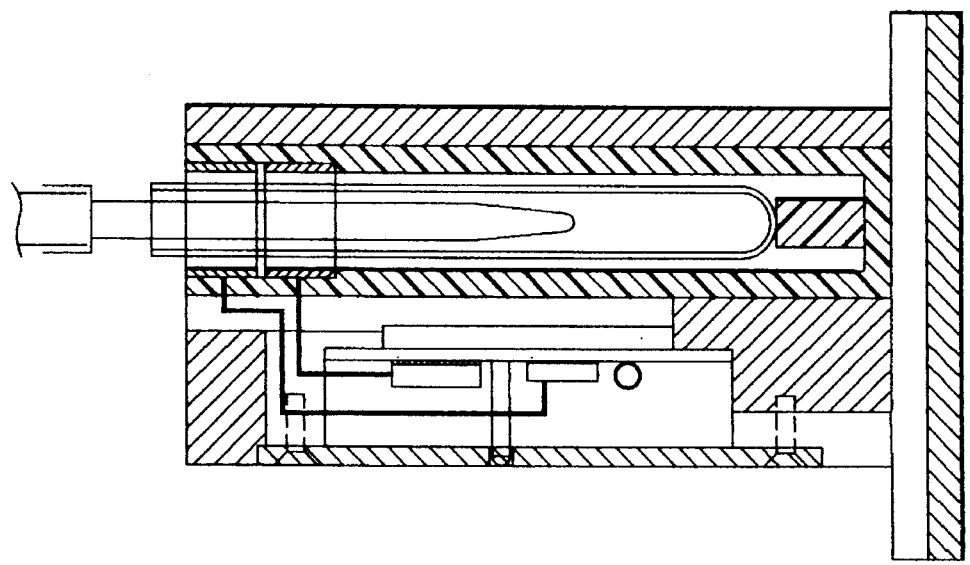
FIGS. 7a to 7c are three schematic diagrams showing various stages of the operation of the capacitative circuit in relation to the position of the probe or pipette tip during calibration of the device and during the detection of liquid in the pipette or probe tip.

The pipette or probe tip 9 is moved into the position shown in FIG. 7a and the computer readout is checked to confirm that no signal indicating the presence of liquid in the pipette to probe tip 9 is indicated by the computer readout.

Figure 7B:
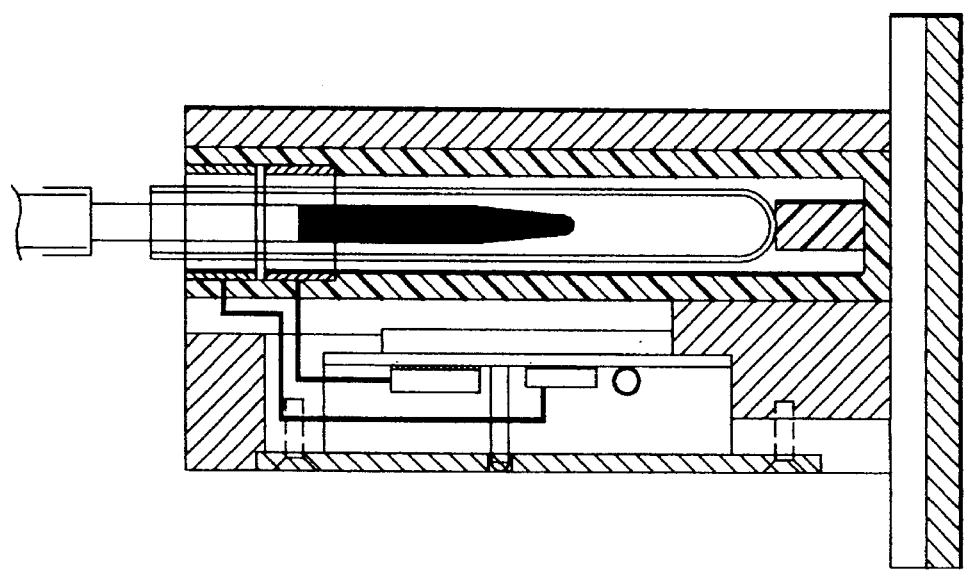

The pipette or probe tip 9 with an incorrect, i.e. insufficient, amount of aspirated liquid, is inserted into the glass tube or vial 10 as shown in FIG. 7b. The capacitative circuit indicates a very slight increase in the output of the operational amplifier (FIG. 6) due to a very slight increase in the resistance presented by the dielectric constant of the capacitative circuit (FIG. 6).

Figure 7C:
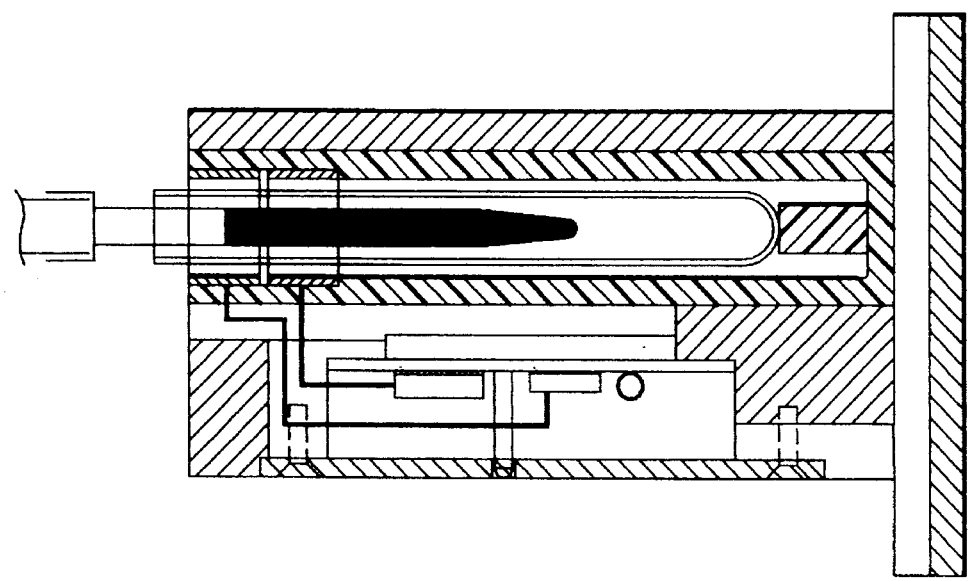
Figure 8A:
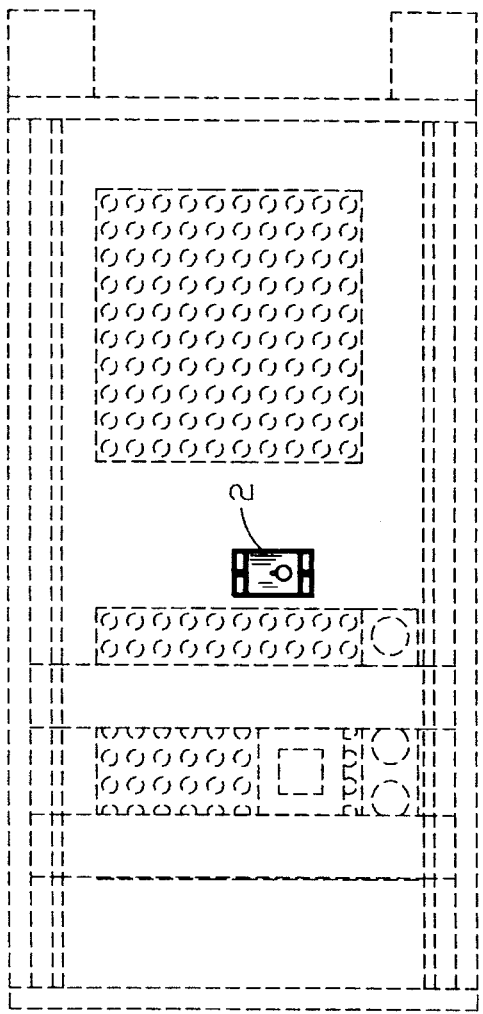
FIG. 8a to 8c are respectively a plan view, a side and a rear elevational view of the volume sensing device of this invention when used in conjunction with a Meltzer Robot.
Figure 8C:
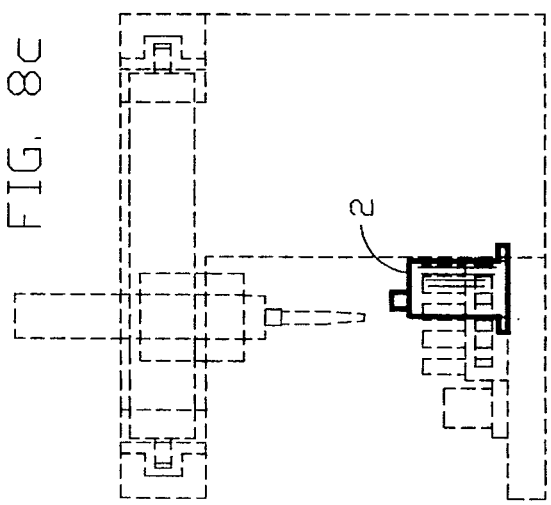
Figure 8B:
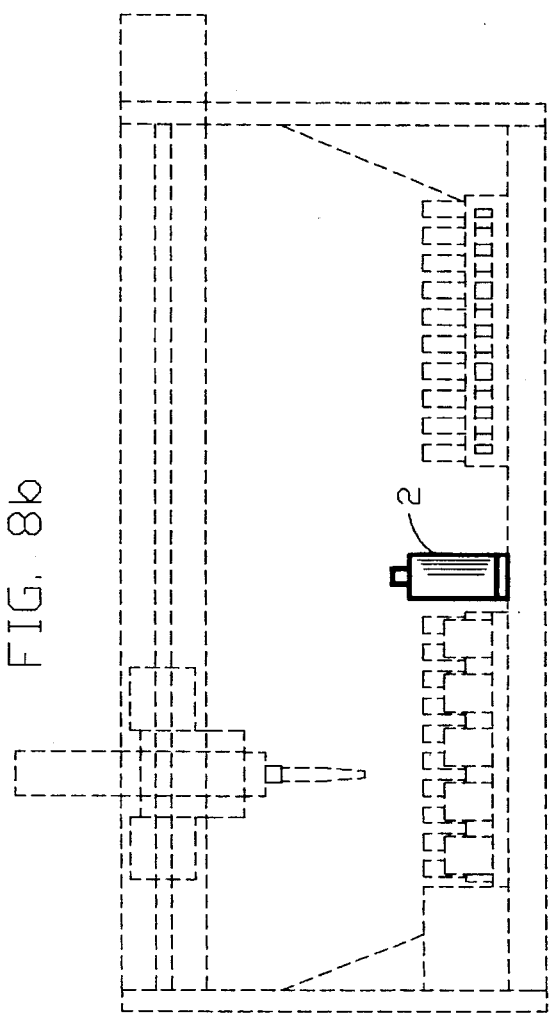

In FIG. 7c the pipette or probe tip 9 holds a correct, i.e. sufficient, amount of liquid which causes a sufficient change in the dielectric constant of the capacitative circuit to cause a sufficient increase in the voltage above the reference voltage to trigger the comparator ( FIG. 6).

Capacitative Circuit

The circuitry for the Liquid Sensing Device consists of six functional parts: a pulse generator 20, the detector assembly 21, an operational amplifier 22, a signal rectifying diode 23, a voltage comparator 24 and an optical coupler 25.

Pulse Generator 20

The pulse generator 20 is a general purpose timer Integrated Circuit NE 555. Values are selected to give a symmetrical square wave operating approximately 25 kilocycles. The acceptable range of working frequencies is fairly broad bat the 25 kilocycles chosen has the advantage of not generating radio interference.

Detector assembly 21

The detector assembly consists physically of two metal rings 4a and 4b fixed in a plastic cylinder 6. The two rings 4a and 4b have very little capacitance because they generally present only as the capacitative resistance (conductivity) area the relatively thin cross-sectional area of the rings. However, when any material which is conductive to electromagnetic waves is introduced inside the rings 4a and 4b the capacitative coupling increases substantially because now the resistance ( conductivity ) area has substantially increased. The ratio between conductivity when no probe or pipette tip containing liquid versus when such a probe or tip is located in the plastic cylinder is important to provide for a high resolution and sensitivity. The output of the pulse generator 20 is connected to the upper ring 4a. The pulses travel from the upper ring 4a, through the liquid in the probe or pipette tip 9 and then to the lower ring 4b which is connected to the input of the operational amplifier 22.

The Operational Amplifier 22

The signal collected at the lower ring 4b is much too weak to be useful. A high low noise amplifier is necessary to make the signal detectable. The signal must also be stable having a consistent amplification factor so that the threshold point between liquid present and liquid not present does not fluctuate. An LM741 I.C. is suitable for this task. A feed back resistor and reference voltage at the positive input add to stability.

The Rectifying Circuit 23

The output of the Operational Amplifier 22 must be converted to direct current so that its value can be compared to a reference voltage. A 1N4001 signal diode with a 0.001 82f capacitor as a filter accomplishes this. The resulting D.C. voltage is in proportion to the amplitude of the output of the Operational Amplifier 22. This voltage is fed to the negative input of the voltage comparator 24.

The Voltage Comparator 24

The change in voltage from the output of the rectifying circuit 23 with no liquid present in the pipette or probe tip 9 and the voltage with only a small volume of liquid present in the pipette or probe tip 9 can be very slight. Therefore a means for detecting a very small change of voltage reliably and converting it an on or off signal is needed. One half of an LM1458 I.C. serves this purpose as a comparator. There are, of course, many other I.C.'s that can also function as comparators (for example many operationl amplifiers I.C.'s can be used as comparators). The LM1458 I.C. was found particularly suitable in its ability to distinguish between voltages with great stability. The output of the rectifier is applied to the negative input of the comparator. The reference voltage is adjusted to be very slightly less than the signal voltage with no liquid present. When the positive input of the comparator is more positive than the negative input, the output of the comparator is high. As the voltage applied to the negative input increases it crosses the threshold and the output of the comparator switches low.

The Optical Isolator (Coupler) 25

Am LED 16 is connected in series with the LED circuit inside the 4N33 Opto-Isolator. When the output of the voltage comparator switches, low current flows through both LED's. this gives a visual indication as well as energizing the photo-transistor in the Opto-Isolator causing its output to go from high to low. This output is used by a computer or any other data storage device as needed.

While the invention has been described in detail by specific reference to preferred embodiments thereof, it is understood that variations and modifications my be made without departing from the true spirit and scope of the invention.

What is claimed is:

1. A volume sensing device for sensing the volume of liquid in a probe or plastic pipette tip, comprising in combination, a) A housing having a vertically disposed cylindrical blind bore which is open at its upper end;

b) a plastic cylinder mounted in said blind bore;

c) a pair of metal rings separated by a gap of predetermined width is coaxially mounted in said blind bore adjacent to the open upper end thereof;

d) capacitative circuit means operatively mounted in said housing, said circuit means include pulse generator means to emit a signal and operational signal amplifier means; said pulse generator means are connected to the upper ring of said pair of metal rings and said operational amplifier means are connected to the lower metal ring of said pair of metal rings; and e) an electrical power source connected to said capacitative circuit means;

whereby when a pipette or probe is axially lowered into said blind bore, said capacitative circuit means indicate the presence or absence of liquid in said pipette or probe by triggering a signal emission.

2. The volume sensing device as set forth in claim 1, wherein the internal diameters of said pair of metal rings and said blind bore are identical and present a uniform internal bore surface.

3. The volume sensing device as set forth in claim 1, including a glass tube coaxially mounted in said plastic cylinder prior to the volume sensing for collecting any liquid which may accidentally be spilled from said pipette or probe during the volume sensing operation.

4. The volume sensing device as set forth in claim 3, wherein said housing forms a parallelepiped and is made of aluminium.

5. The volume sensing device as set forth in claim 4, wherein said capacitative circuit means are mounted on a board which is fixed to said housing by screw means.

6. The volume sensing device as set forth in claim 5, wherein said housing shaped as a parallelepiped has a recess in which said hoard is mounted by said screw means, and a plate covering said recess and being removably and threadably mounted on said housing by a plurality of screws, said plate being removable by threadably unscrewing said plurality of screws.

7. The volume sensing device as set forth in claim 6, wherein said capacitative circuit includes LED means which are energized by said electrical power source via said capacitative circuit means when said signal emission is triggered by said capacitative circuit means.

8. The volume sensing device as set forth in claim 7, wherein said LED means are mounted on said bore, said plate covering said recess has an opening so that when said LED means are energized a light emission from said LED means can be observed through said opening in said plate.

* * * * *